United States Patent [19]

Sakai et al.

[11] 4,068,070
[45] Jan. 10, 1978

[54] α-CYANOAMINE COMPOUNDS AND A PROCESS FOR PRODUCING THE SAME

[75] Inventors: Katsumi Sakai, Kamiichi; Yukio Onogawa, Komae; Yoshitaka Inamoto, Namerikawa; Hiroshi Nakajima, Toyama; Yasuo Fujimoto, Tokyo; Kuniichiro Ohno, Kodaira; Masashi Yoshida, Souka; Shigehito Araki, Tokyo, all of Japan

[73] Assignees: Fuji Chemical Industry Co., Ltd.; Nippon Chemiphar Co., Ltd., Tokyo, both of Japan

[21] Appl. No.: 648,493

[22] Filed: Jan. 12, 1976

Related U.S. Application Data

[62] Division of Ser. No. 495,138, Aug. 6, 1974, Pat. No. 3,962,247.

[30] Foreign Application Priority Data

July 16, 1974 Japan .................. 49-80727
July 16, 1974 Japan .................. 49-80728
July 16, 1974 Japan .................. 49-80729

[51] Int. Cl.$^2$ .................. C07D 295/08; C07D 295/04
[52] U.S. Cl. .................. 542/470; 260/268 CN; 260/239 BC; 424/250
[58] Field of Search .................. 260/240 K, 268 CN

[56] References Cited

U.S. PATENT DOCUMENTS

| | | | |
|---|---|---|---|
| 3,573,291 | 3/1971 | Fauran et al. | 260/240 K |
| 3,594,384 | 7/1971 | Stachel et al. | 260/268 CN |
| 3,773,939 | 11/1973 | Janssen | 260/240 K |
| 3,940,386 | 2/1976 | Szabo et al. | 260/240 K |

FOREIGN PATENT DOCUMENTS

| | | | |
|---|---|---|---|
| 70-29508 | 12/1966 | Japan | 538/469 |
| 332,334 | 10/1958 | Switzerland | 544/402 |
| 1,139,934 | 1/1969 | United Kingdom | 538/469 |

Primary Examiner—Donald G. Daus
Assistant Examiner—D. B. Springer
Attorney, Agent, or Firm—Oblon, Fisher, Spivak, McClelland & Maier

[57] ABSTRACT

α-Cyanoamine compounds represented by the following formula or an acid addition salt thereof

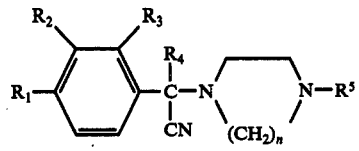

wherein $R_1$ is a halogen atom or lower alkoxy group, $R_2$ and $R_3$ are a hydrogen atom or lower alkoxy group, $R_4$ is a hydrogen atom or lower alkyl group, $R_5$ is a hydrogen atom, —COOR$_6$ ($R_6$ is lower alkyl group),

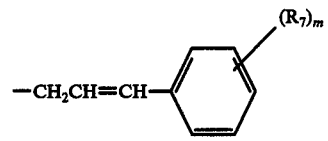

($R_7$ is lower alkoxy group, $m$ is a numeral 0–3), —R$_8$—COOR$_9$ ($R_8$ is lower alkylene group, $R_9$ is lower alkyl group),

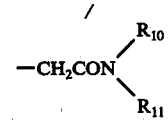

($R_{10}$ and $R_{11}$ are a hydrogen atom or lower alkyl group, or $R_{10}$ and $R_{11}$ jointly form alkylene group), or

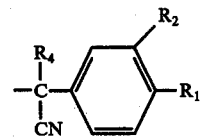

($R_1$ to $R_4$ are the same as defined above) and $n$ is a numeral 2 or 3; but it is excluded when $R_5$ is hydrogen atom or —COOR$_6$ ($R_6$ is the same as defined above) and $n$ is a numeral 2, which are produced by reacting aromatic carbonyl compounds with piperazine or homopiperazine compounds in the presence of hydrogen cyanide or salts thereof, or which are alternatively produced by reaction N-(α-cyanobenzyl)-piperazines of N-(α-cyanobenzyl)homopiperazines or acid addition salts thereof with halogenated compounds.

4 Claims, No Drawings

α-CYANOAMINE COMPOUNDS AND A PROCESS FOR PRODUCING THE SAME

This is a division of application Ser. No. 495,138, filed Aug. 6, 1974, now U.S. Pat. No. 3,962,247 issued June 8, 1977.

BACKGROUND OF THE INVENTION

1. Field of the Invention

This invention relates to N-α-cyanobenzyl piperazine or homopiperazine derivatives and acid addition salts thereof and to a process for producing the same.

2. Description of the Prior Art

Recently, a number of products have been developed in response to a social demand for therapeutic and prophylactic drugs which are effective for treatment of various circulation diseases, such as cerebral and coronary circulation.

Particularly preferred is 2,3,4-trimethoxybenzylpiperazine dihydrochloride, which is currently marketed under the name of Vastarel F (generic name: trimetazidine dihydrochloride). This compound has been shown to be clinically effective as an antianginal drug, and the pharmacological effect has been to increase coronary blood flow and to enhance myocardial metabolism. However, these effects are relatively transitory and the drug has the disadvantage of having a depressant effect on the heart.

SUMMARY OF THE INVENTION

Accordingly, it is one object of this invention to provide novel α-cyanoamine compounds which are effective in the treatment of ischemic heart diseases, particularly angina pectoris, which cause an increase in coronary blood flow and coronary sinus oxygen tension.

It is another object of this invention to provide an industrially acceptable process for producing these novel compounds. These and further objects will become more fully apparent have been attained by the provision of

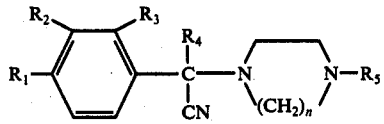
(I)

wherein $R_1$ is a halogen or lower alkoxy, $R_2$ and $R_3$ are hydrogen or lower alkoxy, $R_4$ is hydrogen or lower alkyl, $R_5$ is a hydrogen atom, $-COOR_6$ ($R_6$ is lower alkyl group),

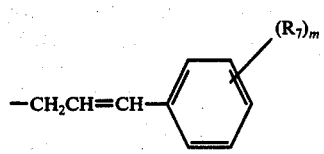

($R_7$ is lower alkoxy group, $m$ is a numeral 0–3), $-R_8-COOR_9$ ($R_8$ is lower alkylene group, $R_9$ is lower alkyl group),

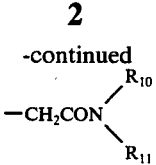

($R_{10}$ and $R_{11}$ are a hydrogen atom or lower alkyl group, or $R_{10}$ and $R_{11}$ jointly form alkylene group), or

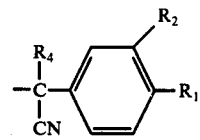

($R_1$ to $R_4$ are the same as defined above), and $n$ is a numeral 2 or 3. This compound has been found to have marked coronary dilating effect and decreasing effect on the work of left ventricle due to hypotensive action. It has further been recognized that these products will exert a long duration of action which increases coronary sinus oxygen tension, produces less toxic effect and has less influence on the central and peripheral nervous system. The term "lower" in qualifying groups and compounds is used herein to mean groups and compounds containing up to 3 carbon atoms.

DETAILED DESCRIPTION OF THE PREFERRED EMBODIMENTS

The present α-cyanoamine compounds represented by the general formula (I) are further divided into the following groups.

The most valuable compounds in the present α-cyanoamine compounds represented by the general formula (I) are as follows:

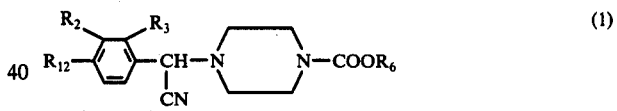

$R_{12}$: lower alkoxy group
$R_2$, $R_3$, $R_6$: same as defined above

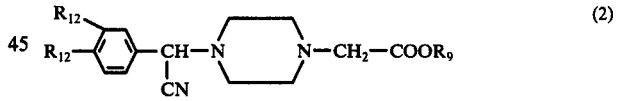

$R_9$: lower alkyl group
$R_{12}$: same as defined above

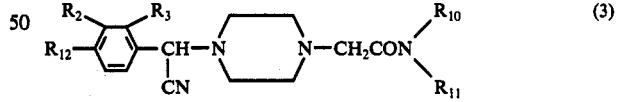

$R_2$, $R_3$, $R_{10}$, $R_{11}$, $R_{12}$: same as defined above

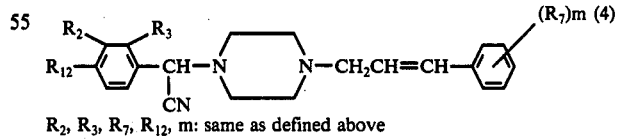

$R_2$, $R_3$, $R_7$, $R_{12}$, m: same as defined above

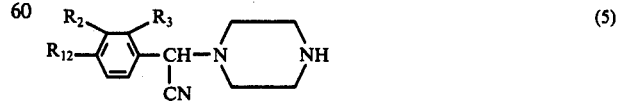

$R_2$, $R_3$, $R_{12}$: same as defined above

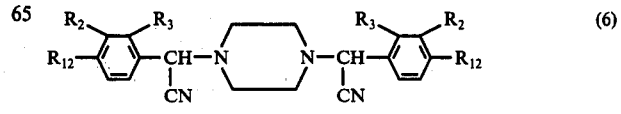

-continued $R_2, R_3, R_{12}$: same as defined above

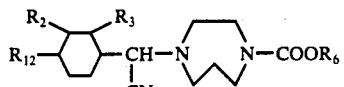 (7)

$R_2, R_3, R_6, R_{12}$: same as defined above

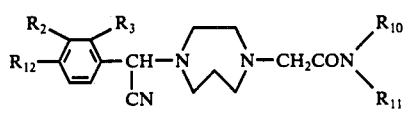 (8)

$R_2, R_3, R_{10}, R_{11}, R_{12}$: same as defined above

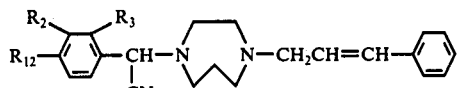 (9)

$R_2, R_3, R_{12}$: same as defined above

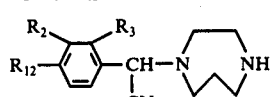 (10)

$R_2, R_3, R_{12}$: same as defined above

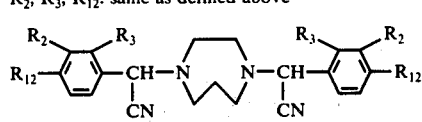 (11)

$R_2, R_3, R_{12}$: same as defined above

According to the present invention, there are provided α-cyanoamine compounds represented by the general formula (I) as follows. That is, according to the following reaction equation α-cyanoamine compounds (I) can be produced by reacting aromatic carbonyl compounds (II) with piperazine or homopiperazine compounds (III) or acid addition salts thereof and hydrogen cyanide (IV) or salts thereof.

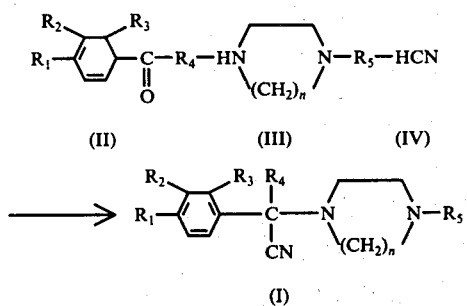

wherein $R_1$ to $R_5$ are the same as defined above.

Namely, the present invention provides a process for producing novel α-cyanoamine compounds through α-cyanoamination of carbonyl compounds by known methods, generally represented by Strecker Reaction. Accordingly, salts of hydrogen cyanide which easily liberate hydrogen cyanide by acids, can also be used in the present invention. This can be achieved by adding equal moles of acid together with piperazine or homopiperazine compounds to said salts. That is, according to the present process, there may be reacted in various forms three starting materials of aromatic carbonyl compounds, piperazine or homopiperazine compounds and hydrogen cyanide. In all cases, the reaction proceeds quantitatively.

Addition of hydrogen cyanide or a salt thereof, piperazine or homopiperazine compounds or acid addition salts thereof, and/or acids can be carried out in any sequence or the starting materials may be added simultaneously. In more detail, the aromatic carbonyl compounds are reacted with piperazine or homopiperazine compounds or acid addition salts thereof, followed by addition of hydrogen cyanide or salts thereof or solution thereof. Alternatively, hydrogen cyanide or a salt thereof is first added to the aromatic carbonyl compound. In this case, acceleration of the reaction may be accomplished by the use of sodium sulfite or sodium hydrogen sulfite. Subsequently, piperazine or a homopiperazine compound is added to the resulting mixture to yield the product in excellent yield. In view of procedural ease and availability of materials, the most industrially convenient process comprises treating the salts of hydrogen cyanide. Preferable salts to be used include those such as potassium, sodium and copper cyanide which easily liberate hydrogen cyanide by the use of an acid.

In the present invention, any inert solvent may be used. Of these, particularly preferred are the polar solvents, such as methanol, ethanol, water of dimethylformamide from the point of view of solubility and reactivity of materials. Mixtures of solvents may also be employed.

The reaction will proceed sufficiently at room temperature, and as the case may be, it is necessary to cool the reactant because of exothermic reaction. The mixture may be heated to accelerate the rate of the reaction with excellent results.

The preferred acid addition salts of piperazine or homopiperazine compounds to be used in the present invention include mineral acid salts thereof such as hydrochloride and hydrobromide. In case free hydrogen cyanide is directly used, the reaction can be carried out while adding a solution containing hydrogen cyanide or absorbing hydrogen cyanide in a solution containing other materials.

An alternative process for producing α-cyanoamine compounds can be represented by the following reaction equation.

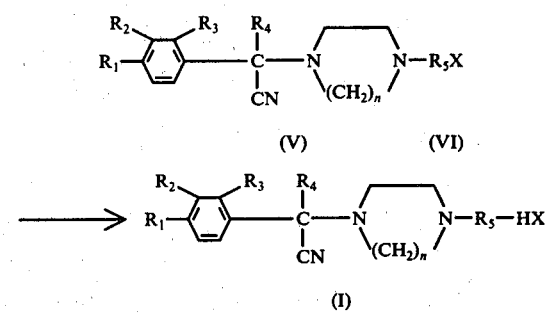

wherein $R_1$ to $R_5$ are the same as defined above, and X is a halogen atom.

That is, N-(α-cyanobenzyl)piperazine or N-(α-cyanobenzyl) homopiperazine represented by the formula (V) is reacted with a halogenated compound represented by the formula (VI) to obtain an α-cyanoamine.

Ordinary solvents can be used in this reaction with the exception of primary and secondary amines. Suitable solvents to be used include, for example, inert aromatic hydrocarbons such as benzene, alkylbenzene and halobenzene, pyridine which may also act as a dehydrohalogenation agent, ethers, such as diethyl ether, tetrahydrofuran and dioxane, alicyclic hydrocarbons such as cyclohexane, ketones such as acetone, and alcohols such as isopropanol, propanol and ethanol. Although the reaction is conducted at room temperature, the reaction may be accelerated by application of heat. It is suitable in this reaction to use as a dehydrohalogenation agent a carbonate or bicarbonate of an alkali metal, or an alkaline earth metal, or a base such as, for example, triethyl amine, N,N-dimethylaniline or pyridine.

The reaction rates are usually high. From a procedural point of view, it may be convenient to add directly a halogenated compound to N-α-cyanobenzyl piperazine or homopiperazine, or to react halogenated compound dissolved in a suitable solvent with said piperazine or homopiperazine compound. On each occasion, the reaction will coincide with the addition of a base or a mixture of bases, and will proceed rapidly to completion.

Reaction temperature and time required for completion will vary, to a slight extent, according to the species of halogenated compound employed. It takes about 2 to 5 hours to complete the reaction sufficiently at ordinary or elevated temperatures.

In an applied embodiment according to the present invention, compounds derived via substitution reaction of corresponding alcohols, such as, for example, dialkyl carbonate and cinnamyl p-toluenesulfonate may be used to yield N-α-cyanobenzyl-N'-alkoxy-carbonyl-piperazine or -homopiperazine and N-α-cyanobenzyl-N'-cinnamyl-piperazine or -homopiperazine, respectively.

The pharmacological effects of typical compounds of the present invention were examined in comparison with those of Vastarel F (generic name: trimetazidine dihydrochloride) being on the market as an antianginal drug. The following compounds were tested.

| Compounds | Structural Formulae |
|---|---|
| Compound A | 3,4-(CH$_3$O)$_2$C$_6$H$_3$-CH(CN)-N(piperazine)N-COOC$_2$H$_5$ |
| Compound B | 3,4-(CH$_3$O)$_2$C$_6$H$_3$-CH(CN)-N(piperazine)N-CH$_2$COOC$_2$H$_5$ |
| Compound C | 3,4-(CH$_3$O)$_2$C$_6$H$_3$-CH(CN)-N(piperazine)N-CH$_2$CON(pyrrolidine) · HCl |
| Compound D | 3,4-(CH$_3$O)$_2$C$_6$H$_3$-CH(CN)-N(piperazine)N-CH$_2$CH=CH-C$_6$H$_5$ · HCl |
| Compound E | 3,4-(CH$_3$O)$_2$C$_6$H$_3$-CH(CN)-N(homopiperazine)N-CH$_2$CH=CH-C$_6$H$_5$ |
| Compound F | 3,4-(CH$_3$O)$_2$C$_6$H$_3$-CH(CN)-N(piperazine)NH · HCl |
| Vastarel F | 2,3,4-(CH$_3$O)$_3$C$_6$H$_2$-CH$_2$-N(piperazine)NH · 2HCl |

All experiments were made on male and female thoractomized mongrel adult dogs weighing about 10 kg. under anesthesia with pentobarbital sodium. Compounds A, D, E and F were suspended in 0.2% CMC solution, Compound B dissolved in hydrochloric acid solution (pH 6), and Compound C and active placebo being dissolved in physiological saline solution. Animals were administered the drug intravenously on brachiuma with either test compound or active placebo.

Arterial blood pressure was measured by pressure transducer (Nippon Koden MPU-0.5) connected with the cannula inserted from exposed carotid artery into aorta. Aortic blood flow was determined by means of electromagnetic flow meter (Nippon Koden MF-5) mounted at the origin of the aorta. Coronary sinus out flow and coronary sinus oxygen tension were assessed by means of electromagnetic flow meter (Nippon Koden MF-5) and P$_{o2}$ macro electrode (Beokmann Moder 160-C), respectively using Morawitz cannulization technique. Heart rate was measured by cardiotachometer (Nippon Koden RT-2) synchronized with systolic blood pressure of aorta.

The work done by the left ventricle is calculated according to the following equation:

The work of the left ventricle (kg/min) = arterial mean blood pressure (mmHg) × aortic blood flow (1/min) × 13.6

1. Effects on arterial mean blood pressure (see Table 1)

Compounds A, C, D and E showed hypotensive effects being proportioned to their doses which were of long duration. Compound B exerted a transitory hypotensive effect immediately after administration, and thereafter increased blood pressure which was then, from 10 minutes after medication, returned to the level before treatment. In animals given compound F, an increase in blood pressure was observed immediately after administration, but thereafter, a long duration hypotensive effect was observed. Vastarel F showed hypotensive effects in proportion to dose, which was relatively transitory.

2. Effects on aortic blood flow (see Table 2)

Compound A increased aortic blood flow by 2-8% during the course of observation period, compounds B, C, D, E and F caused an increase in blood flow immediately after administration, followed by a decrease in blood flow, and Vastarel F decreased markedly the blood flow immediately after medication and thereafter an increase in aortic blood flow was observed.

3. Effects on coronary sinus out flow (see Table 3)

Each of compounds A, B, C, D and E exerted clearly a marked increasing effect on coronary sinus out flow, which was proportioned to doses thereof and of long duration. Compound F increased markedly coronary sinus out flow immediately after administration, effect of which was, however, relatively transitory in comparison with those of aforementioned compounds. On the contrary, Vastarel F caused a decrease in coronary sinus out flow until 1 minute after medication and increased it only to an extremely slight extent from after 5 minutes.

4. Effects on coronary sinus oxygen tension (see Table 4)

Each compound of A, B, C, D and E caused a significant increase in coronary sinus oxygen tension, effect of which was of long duration, and compound F increased oxygen tension by about 20%, effect of which was, however, slightly transitory as compared with those of compounds as mentioned above. On the contrary, Vastarel F caused only a minimum increase in oxygen tension by 3-5% until after 5-20 minutes.

5. Effects on heart rate (see Table 5)

Each compound of A, B, C, D and E showed a slight negative chronotropic effect, on the contrary, compound F and Vastarel F exerted slight negative chronotropic effects accompanied by an increase in heart rate immediately after administration. From these results, particularly from Tables 3 and 4, it might be concluded that the compounds of the present invention increase markedly coronary sinus out flow and coronary sinus oxygen tension, any effects of which are stronger and of longer duration than those of Vastarel F. Moreover, these compounds cause a decrease in the work done by the left ventricle calculated according to the equation as mentioned above, and they have less depressant effects on the heart.

Acute toxicity ($LD_{50}$, per os; mice) of compound A was found to be 2200 mg/kg, on the other hand, Vastarel F 960 mg/kg. Accordingly, it can be presumed that the novel compounds of the present invention may be safely administered to patients with ischemic heart diseases, particularly angina pectoris and provide sure improvements.

Table 1.
Effects on arterial mean blood pressure

| Compounds | Dose (mg/kg) | No. of animals | Initial basal values imm. (mmHg) |  | Changes (%) of basal values | | | | | |
|---|---|---|---|---|---|---|---|---|---|---|
|  |  |  |  |  | 1 | 5 | 10 | 20 | 30 | 40(min.) |
|  | 2.0 | 5 | 104 | −4.0 | −1.5 | −2.6 | −4.2 | −3.8 | −4.5 | — |
| Compound A | 6.0 | 6 | 98 | −4.2 | −3.4 | −5.2 | −6.0 | −5.2 | −3.0 | — |
|  | 20.0 | 5 | 124 | −14.5 | −16.9 | −16.9 | −16.0 | −17.0 | −14.9 | — |
|  | 0.2 | 4 | 108 | −5.0 | +4.8 | +0.4 | +0.1 | −0.1 | 0 | 0 |
| Compound B | 0.6 | 5 | 101 | −14.4 | +6.2 | +0.1 | −0.3 | 0 | 0 | 0 |
|  | 3.0 | 4 | 104 | −16.2 | +7.0 | +2.5 | +0.4 | −1.0 | −0.5 | 0 |
|  | 2.0 | 5 | 102 | −4.2 | +0.8 | 0 | 0 | 0 | 0 | 0 |
| Compound C | 6.0 | 5 | 104 | −12.1 | −3.9 | −1.6 | −0.7 | −3.6 | −2.5 | −1.3 |
|  | 20.0 | 6 | 98 | −29.0 | −17.1 | −18.8 | −22.2 | −27.2 | −28.0 | −26.1 |
|  | 2.0 | 5 | 112 | −13.6 | +1.6 | −3.0 | −1.5 | −0.5 | 0 | 0 |
| Compound D | 6.0 | 5 | 110 | −36.1 | −9.7 | −10.3 | −10.0 | −6.0 | −3.0 | −1.0 |
|  | 20.0 | 4 | 112 | −45.0 | −19.7 | −14.4 | −13.5 | −8.3 | −5.1 | −3.1 |
|  | 2.0 | 4 | 117 | −7.4 | −1.5 | −3.3 | −2.1 | −1.0 | −0.3 | 0 |
| Compound E | 6.0 | 5 | 110 | −22.6 | −3.8 | −6.0 | −10.9 | −8.2 | −3.8 | −2.8 |
|  | 20.0 | 4 | 106 | −29.9 | −8.3 | −15.9 | −21.2 | −19.9 | −16.2 | −11.4 |
|  | 2.0 | 5 | 100 | +2.3 | −1.3 | −4.9 | −3.3 | −2.1 | −0.4 | 0 |
| Compound F | 6.0 | 5 | 97 | +16.0 | +15.8 | −9.3 | −12.5 | −10.0 | −5.2 | −2.8 |
|  | 0.2 | 4 | 94 | −3.0 | −1.0 | −2.0 | −1.5 | 0 | 0 | — |
| Vastarel F | 0.6 | 5 | 96 | −6.0 | −2.0 | −1.5 | −1.0 | 0 | 0 | — |
|  | 2.0 | 4 | 102 | −55.0 | −35.0 | −2.0 | −1.0 | −1.0 | −2.0 | — |

Table 2
Effects on aortic blood flow

| Compounds | Dose (mg/Kg) | No. of animals | Initial basal values imm. (l/min) |  | Changes (%) of basal values | | | | | |
|---|---|---|---|---|---|---|---|---|---|---|
|  |  |  |  |  | 1 | 5 | 10 | 20 | 30 | 40(min.) |
|  | 2.0 | 5 | 1.2 | +0.5 | +4.3 | +3.7 | +2.3 | +1.0 | +1.0 | — |

Table 2-continued

Effects on aortic blood flow

| Compounds | Dose (mg/Kg) | No. of animals | Initial basal values imm. (l/min) | | Changes (%) of basal values | | | | | |
|---|---|---|---|---|---|---|---|---|---|---|
| | | | | | 1 | 5 | 10 | 20 | 30 | 40(min.) |
| Compound A | 6.0 | 6 | 0.7 | +4.3 | +5.8 | +3.7 | +0.1 | −0.2 | +0.2 | — |
| | 20.0 | 5 | 0.8 | +6.1 | +7.3 | +10.2 | +8.0 | +3.3 | +1.0 | — |
| | 0.2 | 4 | 0.7 | +2.5 | +1.2 | +0.3 | −0.1 | 0 | 0 | 0 |
| Compound B | 0.6 | 5 | 0.6 | +4.8 | +1.6 | +2.3 | 0 | −1.1 | −0.7 | 0 |
| | 2.0 | 4 | 0.7 | +6.2 | +4.3 | −1.2 | −2.1 | −1.8 | 0 | 0 |
| | 2.0 | 5 | 0.8 | +1.1 | +2.3 | +0.7 | −1.5 | −0.3 | −0.1 | 0 |
| Compound C | 6.0 | 5 | 0.7 | +8.5 | +3.4 | +1.1 | 0 | −1.0 | −2.0 | −1.1 |
| | 20.0 | 6 | 0.8 | +15.8 | +6.2 | +4.8 | +1.3 | −7.1 | −11.9 | −8.3 |
| | 2.0 | 5 | 0.6 | +8.3 | +3.3 | −0.8 | 0 | 0 | 0 | 0 |
| Compound D | 6.0 | 5 | 0.6 | +12.0 | +3.3 | −2.7 | +0.7 | +0.5 | 0 | 0 |
| | 20.0 | 4 | 0.6 | +27.4 | +16.3 | −3.8 | −4.0 | −3.4 | −1.8 | −0.3 |
| | 2.0 | 4 | 0.8 | +9.9 | +3.6 | +0.8 | 0 | 0 | 0 | 0 |
| Compound E | 6.0 | 5 | 0.8 | +11.7 | +5.8 | 0 | −3.7 | −2.8 | −1.5 | −0.3 |
| | 20.0 | 4 | 0.7 | +16.3 | +7.6 | −4.8 | −12.4 | −10.5 | −9.5 | −7.6 |
| | 2.0 | 5 | 0.6 | +9.2 | +0.7 | −4.1 | −1.2 | 0 | 0 | 0 |
| Compound F | 6.0 | 5 | 0.7 | +20.5 | +12.1 | −2.2 | −2.0 | −1.2 | 0 | 0 |
| | 0.2 | 4 | 0.8 | 0 | 0 | 0 | 0 | 0 | 0 | — |
| Vastarel F | 0.6 | 5 | 0.7 | +1.5 | +0.5 | 0 | −1.0 | −1.0 | 0 | — |
| | 2.0 | 4 | 0.7 | −78.0 | 0 | +11.0 | +23.0 | +5.0 | +5.0 | — |

Table 3.

Effects on coronary sinus out flow

| compounds | Dose (mg/Kg) | No. of animals | Initial basal values imm. (ml/min) | | Changes(%) of basal values | | | | | |
|---|---|---|---|---|---|---|---|---|---|---|
| | | | | | 1 | 5 | 10 | 20 | 30 | 40(min.) |
| | 2.0 | 5 | 36.4 | +10.9 | +7.6 | +5.4 | +4.7 | +4.0 | +3.5 | — |
| Compound A | 6.0 | 6 | 38.0 | +12.0 | +16.6 | +17.0 | +18.0 | +8.5 | +8.0 | — |
| | 20.0 | 5 | 51.6 | +18.5 | +34.3 | +48.3 | +47.1 | +30.0 | +11.8 | — |
| | 0.2 | 4 | 56.0 | +18.0 | +4.9 | +0.7 | 0 | −0.3 | 0 | 0 |
| Compound B | 0.6 | 5 | 64.0 | +39.5 | +30.7 | +0.9 | −0.7 | −0.2 | 0 | 0 |
| | 2.0 | 4 | 75.0 | +55.1 | +47.4 | +8.2 | +5.9 | +3.2 | +1.5 | 0 |
| | 2.0 | 5 | 71.0 | +17.8 | +4.7 | +4.9 | +3.2 | +2.1 | +1.6 | +1.1 |
| Compound C | 6.0 | 5 | 69.0 | +58.2 | +50.7 | +28.6 | +19.4 | +18.2 | +14.3 | +7.6 |
| | 20.0 | 6 | 78.0 | +101.9 | +103.2 | +92.1 | +80.8 | +56.2 | +36.2 | +30.0 |
| | 2.0 | 5 | 56.0 | +6.2 | +1.6 | −3.1 | −1.0 | 0 | 0 | 0 |
| Compound D | 6.0 | 5 | 93.0 | +23.0 | +9.1 | −0.2 | −0.4 | −0.2 | 0 | 0 |
| | 20.0 | 4 | 47.0 | +66.2 | +49.3 | +9.1 | +8.4 | +8.0 | +5.7 | +3.0 |
| | 2.0 | 4 | 65.0 | +7.8 | +2.5 | −0.8 | −1.0 | −0.3 | 0 | 0 |
| Compound E | 6.0 | 5 | 73.0 | +51.3 | +24.3 | +4.2 | +3.3 | +2.3 | +1.5 | +1.1 |
| | 20.0 | 4 | 72.0 | +90.3 | +64.3 | +14.7 | +15.8 | +15.4 | +12.1 | +9.8 |
| | 2.0 | 5 | 48.0 | +12.4 | +2.9 | −1.7 | −4.4 | −3.1 | −1.0 | −0.2 |
| Compound F | 6.0 | 5 | 47.0 | +74.5 | +68.6 | +7.4 | +0.1 | −8.2 | −5.3 | −2.1 |
| | 0.2 | 4 | 30.0 | +4.0 | +1.0 | 0 | 0 | 0 | 0 | 0 |
| Vastarel F | 0.6 | 5 | 68.0 | +6.0 | +2.5 | +0.5 | 0 | 0 | 0 | 0 |
| | 2.0 | 4 | 68.0 | −13.0 | −3.0 | +3.0 | +9.0 | +4.0 | 0 | — |

Table 4.

Effects on coronary sinus oxygen tension

| Compounds | Dose (mg/Kg) | No. of animals | Initial basal values imm. (mmHg) | | Changes(%) of basal values | | | | | |
|---|---|---|---|---|---|---|---|---|---|---|
| | | | | | 1 | 5 | 10 | 20 | 30 | 40(min.) |
| | 2.0 | 5 | 19.1 | +11.2 | +15.2 | +13.8 | +12.5 | +12.0 | +12.0 | — |
| Compound A | 6.0 | 6 | 12.4 | +18.0 | +27.5 | +27.0 | +30.0 | +19.6 | +13.5 | — |
| | 20.0 | 5 | +19.9 | +31.6 | +47.2 | +39.0 | +91.7 | +72.5 | +56.9 | — |
| | 0.2 | 4 | 17.7 | +25.5 | +11.3 | +1.0 | −2.0 | −0.5 | 0 | 0 |
| Compound B | 0.6 | 5 | 17.8 | +68.4 | +46.4 | +8.9 | −3.2 | −0.9 | 0 | 0 |
| | 2.0 | 4 | 19.6 | +80.7 | +70.9 | +26.7 | +8.0 | +3.0 | +0.8 | 0 |
| | 2.0 | 5 | 19.5 | +12.1 | +5.4 | +2.8 | +2.0 | +1.1 | 0 | 0 |
| Compound C | 6.0 | 5 | 18.8 | +36.9 | +29.2 | +22.3 | +19.8 | +15.0 | +14.3 | +12.0 |
| | 20.0 | 6 | 20.6 | +79.1 | +96.2 | +86.7 | +70.4 | +63.7 | +60.9 | +51.5 |
| | 2.0 | 5 | 19.0 | +6.7 | +2.7 | +0.5 | −1.0 | −0.5 | 0 | 0 |
| Compound D | 6.0 | 5 | 16.2 | +23.8 | +14.0 | +5.8 | +1.0 | −1.0 | 0 | 0 |
| | 20.0 | 4 | 18.5 | +60.3 | +43.8 | −21.2 | +8.4 | +3.2 | +2.0 | +0.2 |
| | 2.0 | 4 | 17.6 | +8.3 | +4.1 | +1.1 | +0.5 | 0 | 0 | 0 |
| Compound E | 6.0 | 5 | 16.9 | +29.7 | +27.0 | +8.0 | +8.5 | +4.2 | +2.5 | +0.8 |
| | 20.0 | 4 | 19.5 | +46.2 | +39.2 | +20.4 | +16.6 | +20.8 | +20.2 | +19.8 |
| | 2.0 | 4 | 21.5 | +10.9 | +1.4 | −1.1 | −1.4 | −0.8 | 0 | 0 |
| Compound F | 6.0 | 3 | 20.7 | +20.1 | +20.3 | +3.9 | +1.0 | −4.1 | −1.2 | −0.3 |
| | 0.2 | 4 | 18.5 | +3.0 | +1.0 | 0 | 0 | 0 | 0 | — |
| Vastarel F | 0.6 | 5 | 22.3 | +9.0 | +5.5 | +1.0 | 0 | 0 | 0 | — |
| | 2.0 | 4 | 22.0 | +3.0 | +1.5 | +2.0 | +5.0 | +3.0 | 0 | — |

Table 5.
Effects on heart rate

| Compounds | Dose (mg/Kg) | No. of animals | Initial basal values imm. (beats/min) | | Changes(%) of basal values | | | | | |
|---|---|---|---|---|---|---|---|---|---|---|
| | | | | | 1 | 5 | 10 | 20 | 30 | 40(min.) |
| Compound A | 2.0 | 5 | 184 | −5.2 | −4.7 | −0.6 | −0.4 | 0 | 0 | — |
| | 6.0 | 6 | 186 | −5.0 | −3.9 | −2.3 | −0.9 | +1.0 | +1.0 | — |
| | 20.0 | 5 | 176 | −7.0 | +1.5 | 0 | −1.8 | −6.0 | −6.7 | — |
| Compound B | 0.2 | 4 | 168 | −2.4 | −0.9 | 0 | 0 | 0 | 0 | 0 |
| | 0.6 | 5 | 161 | −13.1 | +0.6 | −0.8 | −0.2 | 0 | −0.5 | 0 |
| | 2.0 | 4 | 160 | −25.3 | −2.4 | −1.5 | −0.7 | 0 | 0 | 0 |
| Compound C | 2.0 | 5 | 166 | −2.8 | +1.1 | +0.3 | −0.2 | 0 | 0 | 0 |
| | 6.0 | 5 | 160 | −5.3 | +5.1 | +1.3 | −0.3 | −1.0 | 0 | 0 |
| | 20.0 | 6 | 151 | −25.6 | +0.8 | +1.6 | −1.0 | −1.4 | −28 | −2.0 |
| Compound D | 2.0 | 5 | 160 | −0.6 | +1.0 | 0 | 0 | 0 | 0 | 0 |
| | 6.0 | 5 | 166 | −1.5 | +1.5 | −0.9 | −1.6 | −1.0 | −0.5 | 0 |
| | 20.0 | 4 | 144 | −14.5 | −3.1 | −3.5 | −3.9 | −2.8 | −1.3 | −0.5 |
| Compound E | 2.0 | 4 | 156 | −2.9 | −0.2 | −0.6 | −1.3 | 0 | 0 | 0 |
| | 6.0 | 5 | 154 | −9.1 | −0.9 | −3.7 | −1.4 | −1.3 | −0.8 | −0.6 |
| | 20.0 | 4 | 141 | −16.8 | −1.0 | −7.8 | −9.1 | −7.9 | −7.1 | −6.6 |
| Compound F | 2.0 | 5 | 125 | +1.4 | +2.6 | −1.5 | −2.3 | −1.8 | −0.7 | 0 |
| | 6.0 | 5 | 122 | −7.2 | +3.7 | −2.2 | −3.6 | −3.3 | −2.0 | −1.4 |
| Vastarel F | 0.2 | 4 | 176 | +1.5 | 0 | −1.5 | −1.0 | 0 | 0 | — |
| | 0.6 | 5 | 150 | +1.5 | +0.5 | −0.5 | 0 | −1.0 | 0 | — |
| | 2.0 | 4 | 150 | +5.5 | −2.0 | −2.0 | −1.5 | −1.5 | −1.5 | — |

The following Examples are given by way of illustration only and are not to be construed as limiting.

EXAMPLE 1

8.3 g. of 3,4-Dimethoxybenzaldehyde was dissolved in 40 ml. of methanol, and 2.5 g. of sodium cyanide in 10 ml. of water was added thereto. .17 g. of Piperazine hydrochloride in 30 ml. of water was added to the resulting mixture and the mixture was stirred at 20° to 21° C. for 3 hours. Separated crystals (by product 2 g.) were filtered off, and the filtrate was concentrated under reduced pressure. To the oily residue was added 20 ml. of water, and the mixture was made alkaline by adding potassium carbonate and extracted with benzene. The extract was dried over sodium sulfate, and then saturated with dry hydrochloric gas. The separated crystals were collected by filtration, and recrystallized from mixture of methanol and diethyl ether to give 12.6 g. of N-(α-cyano-3,4-dimethoxybenzyl)piperazine hydrochloride having a melting point of 195° to 200° C.

| Elemental Analysis: as $C_{14}H_{19}N_3O_2 \cdot HCl \cdot H_2O$ | | | |
|---|---|---|---|
| | C | H | N |
| Calculated (%): | 54.17 | 6.49 | 13.54 |
| Found (%): | 53.86 | 6.49 | 13.95 |

EXAMPLE 2

In a flask was placed 2 G. of 2,3,4-trimethoxybenzaldehyde, 9.9 g. of piperazine hexahydrate, 0.5 g. of sodium cyanide, 5 ml. of methanol and 6 ml. of water to obtain a homogeneous solution. To the resulting solution was added 0.89 ml. of conc. hydrochloric acid. The mixture was stirred for 2.5 hours at 25° to 26° C. The solution was concentrated under reduced pressure and extracted with benzene. The extract was washed with water and reextracted with 10 % hydrochloric acid. The hydrochloric acid solution thus obtained was adjusted to pH 7 with sodium hydroxide solution with cooling, washed with benzene, and extracted with benzene at pH 10–11. This extract was washed with water, dried over medium sulfate, and the solvent was distilled off to give 2.49 g. of N-(α-cyano-2,3,4-trimethoxybenzyl)piperazine as an oily substance. This product was dissolved in ethanol and to the resultant solution was added equal moles of picric acid. This mixture was heated for 10 minutes at 60° C. to be allowed to cool slowly to room temperature, resulting in crystal which was collected by filtration. Recrystallization from ethanol afforded yellow needles having a melting point of 206° to 210° C. (decomposition).

| Elemental Analysis: as $C_{15}H_{21}N_3O_3 \cdot C_6H_3N_3C_7$ | | | |
|---|---|---|---|
| | C | H | N |
| Calculated (%): | 48.46 | 4.65 | 16.15 |
| Found (%): | 48.31 | 4.29 | 16.11 |

EXAMPLE 3

15.75 g. of 3,4-Dimethoxybenzaldehyde and 15.0 g. of N-ethoxycarbonylpiperazine were dissolved in 60 ml. of methanol, and 9.88 g. of conc. hydrochloric acid was added thereto, and then 4.65 g. of sodium cyanide in 30 ml. of water was added dropwise with stirring at a room temperature over a period of 30 minutes. After addition, the resultant mixture, from which crystalline precipitate separated upon heating, was stirred at 50° C. for 2 hours. After cooling, the crystals were collected by filtration, and recrystallized from ligroin to give 30 g. of N-(α-cyano-3,4-dimethoxy-benzyl)-N'-ethoxycarbonylpiperazine having a melting point of 101.0° to 103.5° C.

| Elemental Analysis: as $C_{17}H_{23}N_3O_4$ | | | |
|---|---|---|---|
| | C | H | N |
| Calculated (%): | 64.25 | 6.96 | 12.60 |
| Found (%): | 61.46 | 7.46 | 12.64 |

EXAMPLE 4

2.48 g. of 2,3,4-Trimethoxybenzaldehyde and 2.5 g. of N-ethoxycarbonylpiperazine hydrochloride were dissolved in 10 ml. of methanol, and 0.62 g. of sodium cyanide in 5 ml. of water was added thereto, and then the mixture was stirred at 49° to 50° C. for 2 hours. After completion of the reaction, solvent was distilled off under reduced pressure, and the resultant residue was dissolved in 10 ml. of benzene. The benzene solution was washed with water and dried over sodium sulfate, and then benzene was distilled off to give 4.3 g.

of N-(α-cyano-2,3,4-trimethoxybenzyl)-N'-ethoxycarbonylpiperazine as an oily substance.

The oily substance was dissolved in benzene, and dry hydrochloric acid gas was saturated therein, and then separated cristals were collected by filtration, recrystallized from tetrahydrofuran to give N-(α-cyano-2,3,4-trimethoxybenzyl)-N'-ethoxycarbonylpiperazine hydrochloride having a melting point of 137.5° to 139.0° C.

| Elemental Analysis: as $C_{18}H_{25}N_3O_5$ . HCl | | | |
|---|---|---|---|
| | C | H | N |
| Calculated (%): | 54.07 | 6.55 | 10.51 |
| Found (%): | 54.05 | 6.74 | 10.57 |

EXAMPLE 5

2 g. of 3,4-Dimethoxybenzaldehyde was dissolved in 5 ml. of methanol, and 6 g. of homopiperazine, 0.59 g. of sodium cyanide and 6 ml. of water were added thereto, and then 1.25 g. of conc. hydrochloric acid was added to the resulting mixture. The mixture was stirred at a room temperature for 1 hour, and the completion of the reaction was confirmed by means of Thin-Layer chromatography. The reaction mixture was concentrated under reduced pressure, made alkaline by adding sodium hydroxide with ice cooling, and extracted with benzene. The benzene extract was re-extracted with 10% hydrochloric acid, and the hydrochloric acid extract was neutralized with potassium carbonate and made alkaline with sodium hydroxide, and then extracted with benzene. The extract was dried over sodium sulfate and the solvent was distilled off to give 22 g. of N-(α-cyano-3,4-dimethoxybenzyl)hemopiperazine as an oily substance. The oil was dissolved in acetone, and equimolar amount of oxalic acid in acetone was added thereto, and then separated crystals were collected, recrystallized from mixture of methanol and water to give crystals having a melting point of 195° to 198° C. (decomposition).

| Elemental Analysis: as $C_{15}H_{21}N_3O_2$ . $C_2H_4O_4$ . $2H_2O$ | | | |
|---|---|---|---|
| | C | H | N |
| Calculated (%): | 50.86 | 6.78 | 10.47 |
| Found (%): | 50.54 | 7.05 | 9.85 |

EXAMPLE 6

To the mixture of 12.8 g. of N-ethoxycarbonylpiperazine, 13 ml. of water and 7.1 ml. of 35% hydrochloric acid was added dropwise 10 g. of 4-methoxybenzaldehyde in 40 ml. of methanol at 5° to 10° C. over a period of 5 minutes, and then 3.96 g. of sodium cyanide in 10 ml. of water was added thereto dropwise with stirring at the same temperature over a period of about 30 minutes. The resulting mixture was stirred at 40° C. for 2 hours, and a completion of the reaction was confirmed by means of Thin-Layer chromatography. Solvent was evaporated, and the resultant was dissolved in benzene, washed with diluted hydrochloric acid and water, and then dried over sodium sulfate. Benzene was evaporated to give 19.5 g. of N-(α-cyano-4-methoxybenzyl)-N'-ethoxycarbonylpiperazine as an oily substance. The oil was dissolved in benzene, and dry hydrochloric acid gas was saturated therein, and then separated crystals were collected by filtration, recrystallized from acetone to give N-(α-cyano-4-methoxybenzyl)-N'-ethoxycarbonylpiperazine hydrochloride having a melting point of 170° C.

| Elemental Analysis: as $C_{16}H_{21}N_3O_3$ . HCl | | | |
|---|---|---|---|
| | C | H | N |
| Calculated (%): | 56.55 | 6.53 | 12.37 |
| Found (%): | 56.60 | 6.86 | 12.87 |

EXAMPLE 7

1 g. of 3,4-Dimethoxyphenylethylketone, 1 g. of N-ethoxycarbonylpiperazine hydrochloride, 0.25 g. of sodium cyanide, 2 ml. of ethanol and 6 ml. of water were mixed, and the mixture was stirred at 82° C. for 6 hours. After cooling, 5ml. of water was added to the reaction mixture, and this solution was extracted with benzene. Benzene layer was re-extracted with 10% hydrochloric acid and the extract was washed with benzene, made alkaline by adding sodium hydroxide solution with ice cooling, and extracted with benzene. After drying over sodium sulfate, the extract was evaporated to give 0.32 g. of N-(α-ethyl-α-cyano-3,4-dimethoxybenzyl)-N'-ethoxycarbonylpiperazine as an oily substance.

The oil was dissolved in benzene, dry hydrochloric acid gas was saturated therein, and separated crystals were collected, washed with n-hexane to give crystals having a melting point of 107° to 112° C. Further, the crystals were recrystallized from mixture of tetrahydrofuran and methanol to give N-(α-ethyl-α-cyano-3,4-dimethoxybenzyl)-N'-ethoxycarbonylpiperazine hydrochloride having a melting point of 110° to 113° C.

| Elemental Analysis: as $C_{19}H_{27}N_3O_4$ . HCl | | | |
|---|---|---|---|
| | C | H | N |
| Calculated (%): | 57.30 | 6.79 | 10.56 |
| Found (%): | 56.88 | 6.43 | 10.09 |

EXAMPLE 8

2.56 g. of Cinnamylpiperazine was dissolved in 3 ml. of methanol, and 1.32 g. of 35% hydrochloric acid was added thereto dropwise. To the resulting mixture was added 2.1 g. of 3,4-dimethoxybenzaldehyde in 7 ml. of methanol and then 0.62 g. of sodium cyanide in 5 ml. of water was added dropwise with stirring over a period of 15 minutes. After addition, the mixture was stirred at a room temperature for 2 hours, and then further at 50° C. for 30 minutes so as to complete the reaction. Solvent was evaporated, and the residue was extracted with benzene. The benzene layer was washed with water, dried over sodium sulfate, and benzene was evaporated to give 4.8 g. of crude N-(α-cyano-3,4-dimethoxybenzyl)-N'-cinnamylpiperazine These were recrystallized from ligroin to give 4.3 g. of crystals having a melting point of 119° to 123° C. The crystals were dissolved in benzene, and dry hydrochloric acid gas was saturated therein, and then separated crystals were collected by filtration, recrystallized from methanol to give colourless needles having a melting point of 203° to 204.6° C. (decomposition).

| Elemental Analysis: as $C_{23}H_{27}N_3O_2$ | | | |
|---|---|---|---|
| | C | H | N |
| Calculated (%): | 73.18 | 7.21 | 11.13 |
| Found (%): | 73.31 | 7.35 | 11.33 |

EXAMPLE 9

2 g. of 3,4-Dimethoxyphenylethylketone, 2.08 g. of N-cinnamylpiperazine, 0.51 g. of sodium cyanide, 2 ml. of ethanol and 2 ml. of water were mixed, and 0.38 g. of 35% hydrochloric acid was added thereto, and then the resulting mixture was stirred at 75° to 80° C. for 8 hours. Reaction mixture was concentrated, to which was added water, and extracted with benzene. Benzene layer was reextracted with 10% hydrochloric acid. Separated crystals were extracted with chloroform. Chloroform layer was washed with diluted hydrochloric acid, neutralized with sodium carbonate, dried and chloroform was evaporated to give 1 g. of N-(α-ethyl-α-cyano-3,4-dimethoxybenzyl)-N'-cinnamylpiperazine as an oily substance.

The oil was dissolved in benzene, dry hydrochloric acid gas was saturated therein, and separated crystals were collected by filtration, washed with ether, recrystallized from iso-propanol to give colourless needles having a melting point of about 270° C. (decomposition).

| Elemental Analysis: as $C_{25}H_{31}N_3O_2 \cdot HCl$ | | | |
|---|---|---|---|
| | C | H | N |
| Calculated (%): | 67.87 | 7.24 | 9.50 |
| Found (%): | 68.41 | 7.51 | 9.59 |

EXAMPLE 10

12.4 g. of N-Ethoxycarbonylmethylpiperazine was dissolved in 13 ml. of water, and 2.6 g. of 35% hydrochloric acid was added thereto with ice cooling. 10 g. of 3,4-Dimethoxybenzaldehyde in 40 ml of methanol was added dropwise to resulting mixture at 5° to 10° C. over a period of 10 minutes. To the mixture was added dropwise 3.5 g. of sodium cyanide in 10 ml. of water at the same temperature over a period of 10 minutes, and the mixture was heated at 30° to 40° C. for 2 hours. Reaction mixture was concentrated, and the residue was extracted with benzene, and the extract was washed with water, dried over sodium sulfate, and solvent was evaporated to give 20 g. of crude N-(α-cyano-3,4-dimethoxybenzyl)-N'-ethoxycarbonylmethylpiperazine. It was recrystallized from n-hexane to give 18 g. of scaly crystals having a melting point of 93° to 95° C.

| Elemental Analysis: as $C_{18}H_{25}N_3O_4$ | | | |
|---|---|---|---|
| | C | H | N |
| Calculated (%): | 62.23 | 7.25 | 12.10 |
| Found (%): | 62.73 | 7.47 | 12.23 |

EXAMPLE 11

10 g. of N-Pyrrolidinocarbonylmethylpiperazine was added to 13 ml. of water, and 1.85 g. of 35% hydrochloric acid was added dropwise thereto with ice cooling. 9.3 g. of 3,4-Dimethoxybenzaldehyde in 40 ml. of methanol was added to the resulting mixture, and then 2.5 g. of sodium cyanide in 10 ml. of water was added thereto with stirring at a room temperature over a period of 10 minutes. The mixture was stirred at 35° to 40° C. for 2 hours so as to complete the reaction. Reaction mixture was concentrated, the resultant was extracted with benzene, and the extract was washed with water, dried over sodium sulfate, and solvent was evaporated to give 16 g. of N-(α-cyano-3,4-dimethoxybenzyl)-N'-pyrrolidinocarbonylmethylpiperazine as an oily substance. The oil was dissolved in benzene, dry hydrochloric acid gas was saturated therein, and separated crystals were collected by filtration, recrystallized from isopropanol to give 14 g. of crystals having a melting point of 155° to 157° C.

| Elemental Analysis: as $C_{20}H_{28}N_4O_3 \cdot HCl \cdot H_2O$ | | | |
|---|---|---|---|
| | C | H | N |
| Calculated (%): | 56.27 | 7.32 | 13.12 |
| Found (%): | 56.56 | 7.57 | 13.30 |

EXAMPLE 12

2 g. of 3,4-Dimethoxyphenylethylketone, 1.91 g. of N-(diethylaminocarbonylmethyl)piperazine, 0.51 g. of sodium cyanide, 2 ml. of ethanol and 2 ml. of water were mixed, and 0.9 ml. of 35% hydrochloric acid was added thereto, and then the resulting mixture was stirred under reflux at about 70° C. for 6.5 hours. Reaction mixture was concentrated under reduced pressure, and to the residue was added 10 ml. of water. The mixture was extracted with 20 ml. of benzene. Benzene layer was re-extracted with 10% hydrochloric acid, the hydrochloric acid layer was adjusted to pH 7, and extracted again with benzene. After benzene extract was dried over sodium sulfate, solvent was evaporated to give 1.2 g. of N-(α-ethyl-α-cyano-3,4-dimethoxybenzyl)-N'-diethylaminocarbonylmethylpiperazine as an oily substance. The oil was dissolved in benzene, dry hydrochloric acid gas was saturated therein, and separated crystals were collected by filtration, washed with diethyl ether, and recrystallized from iso-propanol to give crystals having a melting point of about 247° C. (decomposition).

| Elemental Analysis: as $C_{22}H_{34}N_4O_3 \cdot HCl$ | | | |
|---|---|---|---|
| | C | H | N |
| Calculated (%): | 60.14 | 7.97 | 12.76 |
| Found (%): | 59.78 | 7.79 | 12.31 |

EXAMPLE 13–25

The procedure of Examples 1 to 12 were repeated under the conditions described below, there were obtained the following results.

| | Reaction Conditions and Yields | | | | |
|---|---|---|---|---|---|
| | | Reaction Conditions | | | |
| Ex. No. | Compounds | Method | Reaction temp. (° C.) | Reaction time (hour) | Yield (%) |
| 13 | N-(α-cyano-2,3,4-trimethoxybenzyl)-homopiperazine | Exp. 5 | room temp. | 1 | 63 |
| 14 | N-(α-cyano-4-chlorobenzyl)-N'-ethoxycarbonyl- | Exp. 6 | 40 | 3 | 80 |

-continued

Reaction Conditions and Yields

| Ex. No. | Compounds | Method | Reaction temp. (° C.) | Reaction time (hour) | Yield (%) |
|---|---|---|---|---|---|
| 15 | N-(αmethyl-α-cyano-3,4-dimethoxybenzyl)-N'-ethoxycarbonyl-piperazine | Exp. 7 | 82 | 6 | 41 |
| 16 | N-(α-cyano-3,4-dimethoxybenzyl)-N'-ethoxycarbonyl-homopiperamine | Exp. 6 | room temp. to 40 | 2 | 72 |
| 17 | N-(αcyano-2,3,4-trimethoxybenzyl)-N'-ethoxycarbonyl-homopiperazine | Exp. 6 | room temp. to 40 | 3.5 | 96 |
| 18 | N-(αcyano-2,3,4-trimethoxybenzyl)-N'-cinnamylpiperazine | Exp. 8 | room temp. to 50 | 3 | 93.3 |
| 19 | N-(α-cyano-3,4-dimethoxybenzyl)-N'-(4-methoxycinnamyl)-piperazine | Exp. 8 | 40 | 2.5 | 80.9 |
| 20 | N-(αcyano-3,4-dimethoxybenzyl)N'-(2,3,4-trimethoxycinnamyl)piperazine | Exp. 8 | room temp. | 4.0 | 68.5 |
| 21 | N-(α-cyano-3,4-dimethoxybenzyl)-N'-cinnamylhomopiperazine | Exp. 8 | 25 – 50 | 1.5 | 89.1 |
| 22 | N-(α-cyano-2,3,4-trimethoxybenzyl)-N'-cinnamylhomopiperazine | Exp. 8 | 30 – 35 | 1.5 | 95.0 |
| 23 | N-(αcyano-3,4-dimethoxybenzyl)-N'-diethylaminocarbonyl-methylpiperazine | Exp. 11 | room temp. | 3 | 71.8 |
| 24 | N-(α-cyano-3,4-dimethoxybenzyl)-N'-pyrrolidinocarbonyl-methylhomopiperazine | Exp. 11 | room temp. | 3 | 60.5 |
| 25 | N-(α-cyano-3,4-dimethoxybenzyl)-N'-aminocarbonylmethyl-piperazine | Exp. 11 | room temp. | 3 | 62.0 |

Physical Properties

| Ex. No. | Compounds | Formula | Elemental Analysis Calculated (Found) C | H | N | Melting point (° C.) | HMR $\tau$ in CDCl$_3$ >CH—CN | IR (cm$^{-1}$) $\nu$C≡N |
|---|---|---|---|---|---|---|---|---|
| 13 | N-(α-cyano-2,3,4-trimethoxybenzyl)-homopiperazine | $C_{16}H_{23}N_3O_3$ | — | — | 13.76 (13.15) | 260–265 (Picrate) | 4.91 | 2200 |
| 14 | N-(α-cyano-4-chlorobenzyl)-N'-ethoxycarbonyl-piperazine | $C_{15}H_{18}N_3O_2$ Cl . HCl | 52.34 (52.28) | 5.56 (5.61) | 12.21 (12.27) | 166 (hydrochloride) | 5.20 | 2210 |
| 15 | N-(α-methyl-α-cyano-3,4-dimethoxybenzyl)-N'-ethoxycarbonylpiperazine | $C_{18}H_{25}N_3O_4$ . HCl | 56.27 (55.78) | 6.51 (6.42) | 10.94 (10.41) | — | None | 2210 |
| 16 | N-(α-cyano-3,4-dimethoxybenzyl)-N'-ethoxycarbonyl-homopiperzine | $C_{18}H_{25}N_3O_4$ | — | — | 12.10 (11.36) | — | 5.15 | 2210 |
| 17 | N-(α-cyano-2,3,4-trimethoxybenzyl)-N'-ethoxycarbonyl-homopiperazine | $C_{19}H_{27}N_3O_5$ | — | — | 11.13 (10.57) | — | 4.89 | 2200 |
| 18 | N-(α-cyano-2,3,4-trimethoxybenzyl)-N'-cinnamylpiperazine | $C_{24}H_{29}N_3$ | 64.92 (64.84) | 6.81 (6.87) | 9.47 (9.34) | 169–174 (hydrochloride) | 4.99 | 2210 |
| 19 | N-(α-cyano-3,4-dimethoxybenzyl)-N'-(4'methoxycinnamyl)-piperazine | $C_{24}H_{29}N_3O_3$ . HCl | 64.92 (65.08) | 6.81 (6.91) | 9.47 (9.52) | 203–206 (hydrochloride) | — | 2210 |
| 20 | N-(α-cyano-3,4-dimethoxybenzyl)-N'-(2',3',4'-trimethoxycinnamyl)piperazine | $C_{26}H_{33}N_3O_5$ . $C_6H_3N_3O_7$ (Picrate) | — | — | 12.06 (13.31) | Ca: 115–120 (picrate) | — | 2210 |
| 21 | N-(α-cyano-3,4-dimethoxybenzyl)-N'-cinnamylhomopiperzine | $C_{24}H_{29}N_3C_2$ | 73.62 (74.10) | 7.47 (7.93) | 10.73 (10.55) | 100–103 | 5.17 | 2230 |
| 22 | N-(α-cyano-2,3,4-trimethoxybenzyl)-N'-cinnamylhomopiperazine | $C_{25}H_{31}N_3O_3$ . HCl | 65.50 (65.18) | 6.99 (7.33) | 9.17 (9.01) | — | 4.92 | 2220 |
| 23 | N-(α-cyano-3,4-dimethoxybenzyl)-N'-diethylaminocarbonyl-methylpiperazine | $C_{20}H_{30}N_4O_3$ | 64.14 (64.31) | 8.08 (8.40) | 14.96 (15.12) | 130–131 | 5.17 | 2200 |
| 24 | N-(α-cyano-3,4-dimethoxybenzyl)-N'-pyrrolidinocarbonyl-methylhomopiperazine | $C_{21}H_{30}N_4O_3$ | — | — | 14.50 (13.99) | — | 5.16 | 2210 |
| 25 | N-(α-cyano-3,4-dimethoxybenzyl)-N'-aminocarbonylmethyl-piperazine | $C_{16}H_{22}N_4O_3$ | 60.36 (60.23) | 6.97 (6.81) | 17.60 (17.59) | 185–187 | — | 2210 |

EXAMPLE 26

In a 300-ml. three necked flask was placed 4.9 g. of sodium cyanide and 10 ml. of water to obtain a homogeneous solution. To the resuting solution was added 16.6 g. of 3,4-dimethoxybenzaldehyde dissolved in 40 ml. of methanol and then a solution of 9.7 g. of piperazine hexahydrate and 7.95 g. of piperazine dihydrochloride in 30 ml. of water. The reaction mixture, from which crystalline precipitate separated upon heating, was stirred for about 1 hour at 60° C. After the mixture was cooled, crystal to separate was collected by filtration, washed with water and methanol, and dried. There was obtained 22.8 g. of crystal having a melting point of 216°-218.5° C. Recrystallization from chloroform-methanol afforded N,N'-bis-(α-cyano-3,4-dimethoxybenzyl)piperazine as a crystalline product melting at 216°-218° C.

| Elemental Analysis: as $C_{24}H_{28}N_4O_4$ | | | |
|---|---|---|---|
| | C | H | N |
| Calculated (%): | 66.03 | 6.47 | 12.84 |
| Found (%): | 65.74 | 6.36 | 11.71 |

EXAMPLE 27

In a 100-ml. flask was placed 1.59 g. of piperazine dihydrochloride and 3 ml. of water. To the resulting solution was added 3.92 g. of 2,3,4-trimethoxybenzaldehyde dissolved in 15 ml. of methanol. A solution of 0.98 g of sodium cyanide in 5 ml. of water was added dropwise to the mixture over a period of about 10 minutes with ice cooling. Then the reaction mixture, from which crystalline precipitate separated upon heating, was stirred for 2.5 hours while the external temperature was kept at 40° to 50° C. After the mixture was cooled, crystal was collected by filtration, washed with water and methanol, and dried. There was obtained 4.3 g. of crystal having a melting point of 244°-247° C. Recrystallization from chloroform-methanol afforded N,N'-bis-(α-cyano-2,3,4-trimethoxybenzyl)piperazine as a crystalline product melting at 245°-247° C.

| Elemental Analysis: as $C_{26}H_{32}N_4O_6$ | | | |
|---|---|---|---|
| | C | H | N |
| Calculated (%): | 62.89 | 6.50 | 11.28 |
| Found (%): | 62.58 | 6.41 | 11.32 |

EXAMPLE 28

In a flask was placed 0.59 g. of homopiperazine and 3 ml. of water. To the resulting solution was added 1.31 g. of conc. hydrochloric acid with ice cooling, and then 2 g. of 3,4-dimethoxybenzaldehyde dissolved in 5 ml. of methanol. The reaction mixture, from which crystalline precipitate separated upon heating, was stirred for 1 hour at 40°-45° C. After the mixture was cooled, crystal to separate was collected by filtration, washed with water and methanol, and dried. There was obtained 2.3 g. of crystal having a melting point of 140°-142° C. Recrystallization from methanol afforded N,N'-bis-(α-cyano-3,4-dimethoxybenzyl) homopiperazine as a colorless columnar crystal melting as 140°-143° C.

| Elemental Analysis: as $C_{25}H_{30}N_4O_4$ | | | |
|---|---|---|---|
| | C | H | N |
| Calculated (%): | 66.56 | 6.71 | 12.44 |
| Found (%): | 66.71 | 6.79 | 12.37 |

EXAMPLE 29

To 0.5 g. of homopiperazine was added 1.1 g. of conc. hydrochloric acid with cooling, and then 2.0 g. of 2,3,4-trimethoxybenzaldehyde dissolved in 10 ml. of methanol. A solution of 0.5 g. of sodium cyanide in 5 ml. of water was added dropwise to the mixture over a period of about 5 minutes. Then the reaction mixture, from which crystalline precipitate separated immediately after warming, was stirred for 1 hour at 30°-33° C. After the mixture was cooled, crystal was collected by filtration, washed with water, and dried. There was obtained 2.6 g. of crystal having a melting point of 170°-175° C. Recrystallization from methanol afforde 2.3 g. of N,N'-bis-(α-cyano-2,3,4-trimethoxybenzyl)-homopiperazine as a crystalline product melting at 173°-176° C.

| Elemental Analysis: as $C_{27}H_{34}N_4O_6$ | | | |
|---|---|---|---|
| | C | H | N |
| Calculated (%): | 63.51 | 6.71 | 10.97 |
| Found (%): | 63.64 | 6.79 | 10.78 |

EXAMPLE 30

13 g. of N-(α-cyano-3,4-dimethoxybenzyl)piperazine was dissolved in 50 ml. of isopropanol and to the resultant solution was added 7 g. of potassium carbonate. To the mixture was added dropwise 6 g. of ethyl chloroformate dissolved in 10 ml. of isopropanol over a period of about 30 minutes with ice cooling, while the mixture was agitated. After dropping, the ice bath was set apart and the mixture was stirred for 10 minutes at room temperature. The solution was filtered and the filtrate was concentrated under reduced pressure to give 13 g. of N-(α-cyano-3,4-dimethoxybenzyl)-N'-ethoxycarbonylpiperazine.

| Elemental Analysis: as $C_{17}H_{23}N_3O_4$ | | | |
|---|---|---|---|
| | C | H | N |
| Calculated (%): | 61.25 | 6.96 | 12.60 |
| Found (%): | 61.32 | 7.35 | 12.74 |

This product was dissolved in benzene and the resultant solution was saturated with dry hydrochloric gas to separate crystal which was collected by filtration. Recrystallization from tetrahydrofuran afforded crystal having a melting point of 134° C.

EXAMPLE 31

14.5 g. of N-(α-cyano-2,3,4-trimethoxybenzyl)piperazine was dissolved in 50 ml. of anhydrous diethyl ether and to the resultant solution was added 4 g. of pyridine. To the mixture was added dropwise 6 g. of ethyl chloroformate dissolved in 10 ml. of anhydrous diethyl ether over a period of about 30 minutes with ice cooling while the internal temperature was kept at 10°-15° C. The mixture was further stirred at room temperature and filtered off to separate an insoluble matter. The filtrate was evaporated to give crude N-(α-cyano-2,3,4-trimethoxybenzyl)-N'-ethoxycarbonylpiperazine as an oily substance. This product was dissolved in toluene and the resultant solution was saturated with dry hydrochloric gas to separate crystal which was collected by filtration. Recrystallization from tetrahydrofuran-methanol afforded 14 g. of crystal having a melting point of 137.5°–139.0° C.

Elemental Analysis: as $C_{18}H_{25}N_3O_5 \cdot HCl$

|  | C | H | N |
|---|---|---|---|
| Calculated (%): | 54.07 | 6.55 | 10.51 |
| Found (%): | 54.05 | 6.74 | 10.57 |

EXAMPLE 32

In a 100-ml. three necked flask was placed 11.5 g. of N-(α-cyano-4-methoxybenzyl)piperazine and 40 ml. of methanol to obtain a homogenous solution. To the resulting solution was added dropwise 5.96 g. of ethyl chloroformate over a period of about 70 minutes with stirring while the temperature was kept at about 20° C. After dropping, the internal temperature was raised to 40° to 45° C., and then the mixture was further stirred for 2 hours. The solution was concentrated under reduced pressure and 500 ml. of water was added thereto. This solution was made alkaline with the aid of sodium carbonate with cooling and extracted with benzene. The benzene layer was washed with dilute hydrochloric acid and water, and dried over sodium sulfate. The solvent was distilled off to afford 9.7 g. of N-(α-cyano-4-methoxybenzyl)-N'-ethoxycarbonylpiperazine as an oily substance. This product was dissolved in benzene and the resultant solution was saturated with dry hydrochloric gas to separate crystal which was collected by filtration. Recrystallization from acetone afforded N-(α-cyano-4-methoxybenzyl)-N'-ethoxycarbonylpiperazine hydrochloride having a melting point of 170° C.

Elemental Analysis: as $C_{16}H_{21}N_3O_3 HC$

|  | C | H | N |
|---|---|---|---|
| Calculated (%): | 56.55 | 6.53 | 12.37 |
| Found (%): | 56.60 | 6.86 | 12.87 |

EXAMPLE 33

To 11.7 g. of N-(α-cyano-4-chlorobenzyl)piperazine was added 70 ml. of benzene and then 6.9 g. of anhydrous potassium carbonate. To the resulting solution was added dropwise 5.4 g. of ethyl chloroformate dissolved in 30 ml. of benzene with cooling. After dropping, the mixture was stirred for 2 hours at 40°–45° C. After cooling, water was poured into the mixture to dissolve inorganic substance. The benzene layer was separated, washed with water, dried over sodium sulfate, and the solvent distilled off. There was obtained 10.7 g. of N-(α-cyano-4-chlorobenzyl)-N'-ethoxycarbonylpiperazine as an oily substance. This product was dissolved in benzene and the resultant solution was saturated with dry hydrochloric gas to separate crystal which was collected by filtration. Recrystallization from acetone afforded N-(α-cyano-4-chlorobenzyl)-N'-ethoxycarbonylpiperazine hydrochloride having a melting point of 166° C.

Elemental Analysis: as $C_{15}H_{18}N_3O_2Cl \cdot HCl$

|  | C | H | N |
|---|---|---|---|
| Calculated (%): | 52.34 | 5.56 | 12.21 |
| Found (%): | 52.28 | 5.61 | 12.27 |

EXAMPLE 34

To 3.6 g. of N-(α-cyano-3,4-dimethoxybenzyl)piperazine was added 8 ml. of benzene and then 1.47 g. of soda ash. To the resulting mixture was added 2.53 g. of cinnamyl chloride over a period of about 1 hour while the mixture was heated under reflux with stirring. After dropping, the mixture was further refluxed with stirring for 2 hours. After cooling, the mixture was filtered and the filtrate was washed with water and dried over sodium sulfate. The solvent was distilled off under reduced pressure. To the residue was added ligroin to be allowed to stand to give crystal which was collected by filtration. The product was recrystallized from ligroin to give 3.4 g. of crystal having a melting point of 119°–123° C. This crystal was dissolved in benzene and the resultant solution was saturated with dry hydrochloric gas to separate crystal which was collected by filtration. Recrystallization from methanol afforded N-(α-cyano-3,4-dimethoxybenzyl)-N'-cinnamyl piperazine dihydrochloride as needles melting at 203°–204.6° C. (decomposition).

Elemental Analysis: as $C_{23}H_{27}N_3O_2$

|  | C | H | N |
|---|---|---|---|
| Calculated (%): | 73.18 | 7.21 | 11.13 |
| Found (%): | 73.31 | 7.35 | 11.33 |

EXAMPLE 35

To 13 g. of N-(α-cyano-3,4-dimethoxybenzyl)piperazine was added 70 ml. of benzene and then 4 g. of pyridine. To the resulting solution was added 6.3 g. of ethyl chloroacetate over a period of about 10 minutes with ice cooling while the mixture was stirred. After dropping, the mixture was was heated at 30° to 40° C. with stirring for 1 hour, and further refluxed for 1 hour. After cooling, 10 ml. of water was poured into the mixture to separate benzene layer which was washed with water and dried over sodium sulfate. The solvent was distilled off under reduced pressure. To the rosidue was added n-hexane to be allowed to stand to give crystal which was collected by filtration. Recrystallization from n-hexane afforded 8.5 g. of N-(α-cyano-3,4-dimethoxybenzyl)-N'-ethoxycarbonylmethylpiperazine as a squamous crystal havin a melting point of 93°–95° C.

Elemental Analysis: as $C_{18}H_{25}N_3O_4$

|  | C | H | N |
|---|---|---|---|
| Calculated (%): | 62.23 | 7.25 | 12.10 |
| Found (%): | 62.73 | 7.47 | 12.23 |

EXAMPLE 36

To 17.7 g. of N-(α-cyano-3,4-dimethoxybenzyl)piperazine was added 60 ml. of benzene and then 5.3 g. of pyridine. To the resulting solution was added dropwise 7.9 g. of pyrrolidylcarbonylmethyl chloride dissolved in 20 ml. of benzene over a period of about 10 minutes with stirring at room temperature. After dropping, the temperature was raised slowly and the mixture to separate benzene layer which was washed with water and dried over sodium sulfate. The solvent was distilled off to give 15 g. of N-(α-cyano-3,4-dimethoxybenzyl)-N'-pyrrolidinocarbonylmethylpiperazine as an oily substance. This product was dissolved in benzene and the resultant solution was saturated with dry hydrochloric gas to separate crystal which was collected by filtration. Recrystrallization from iso-propanol afforded N-(α-cyano-3,4-dimethoxybenzyl)-N'-pyrrolidinocarbonyl-methylpiperazine hydrochloride monohydrate having a melting point of 155° to 157° C.

| Elemental Analysis: as $C_{20}H_{28}N_4O_3$ | | | |
|---|---|---|---|
| | C | H | N |
| Calculated (%): | 56.27 | 7.32 | 13.12 |
| Found (%): | 56.56 | 7.57 | 13.30 |

EXAMPLES 37–50

The procedure of Examples were repeated under the conditions described below, there were obtained the following results.

Reaction Conditions and Yields

| Ex. No. | Compounds | Method | Reaction Temp. (° C) | Reaction Time (hour) | Yield (%) |
|---|---|---|---|---|---|
| 37 | N-(α-methyl-α-cyano-3,4-dimethoxybenzyl)-N'-ethoxycarbonyl-piperazine | 33 | room temp. to 45 | 2.0 | 48.0 |
| 38 | N-(α-ethyl-α-cyano-3,4-dimethoxybenzyl)-N'-ethoxycarbonyl-piperazine | 33 | room temp. to 45 | 2.0 | 25 |
| 39 | N-(α-cyano-3,4-dimethoxybenzyl)-N'-ethoxycarbonyl-homopiperazine | 33 | room temp. to 80 | 3.0 | 40 |
| 40 | N-(α-cyano-2,3,4-trimethoxybenzyl)-N'-ethoxycarbonyl-homopiperazine | 33 | room temp. to 80 | 3.0 | 40 |
| 41 | N-(α-cyano-2,3,4-trimethoxybenzyl)-N'-cinnamylpiperazine | 34 | 75 to 80 | 3.0 | 68.0 |
| 42 | N-(α-cyano-3,4-dimethoxybenzyl)-N'-(4'-methoxycinnamyl)piperazine | 34 | 70 to 80 | 3.0 | 65.0 |
| 43 | N-(α-cyano-3,4-dimethoxybenzyl)-N'-(2',3',4'-trimethoxycinnamyl)-piperazine | 34 | 70 to 80 | 3.0 | 71.0 |
| 44 | N-(α-cyano-3,4-dimethoxybenzyl)-N'-cinnamyl-homopiperazine | 34 | 70 to 80 | 3.0 | 67.5 |
| 45 | N-(α-cyano-2,3,4-trimethoxybenzyl)-N'-cinnamyl-homopiperazine | 34 | 70 to 80 | 3.0 | 60.0 |
| 46 | N-(α-ethyl-α-cyano-3,4-dimethoxy)-N'-cinnamylpiperazine | 34 | 70 to 80 | 3.0 | 43.0 |
| 47 | N-(α-cyano-3,4-dimethoxybenzyl)-N'-diethylaminocarbonyl-methylpiperazine | 36 | room temp. to 80 | 1.5 | 53.0 |
| 48 | N-(α-cyano-3,4-dimethoxybenzyl)-N'-pyrrolino-carbonylmethyl-homopiperazine | 36 | room temp. to 80 | 1.5 | 58.0 |
| 49 | N-(α-cyano-3,4-dimethoxybenzyl)-N'-aminocarbonylmethyl piperazine | 36 | room temp. to 50 | 1.5 | 21.0 |
| 50 | N-(α-ethyl-α-cyano-3,4-dimethoxybenzyl)-N'-diethylamino-carbonylmethyl piperazine | 36 | room temp. to 80 | 1.5 | 30 |

Physical Properties

| Example No. | Compounds | Formula | Elemental Analysis Calculated (Found) C | H | N | Melting Point (° C) | NMR (τ in CDCl₃) >CH—CN | IR (cm⁻¹) νC≡N |
|---|---|---|---|---|---|---|---|---|
| 37 | N-(α-methyl-α-cyano-3,4-dimethoxybenzyl)-N'-ethoxycarbonyl piperazine | $C_{18}H_{25}N_3O_4$ HCl | 56.27 (55.78) | 6.51 (6.42) | 10.94 (10.41) | — | None | 2210 |
| 38 | N-(α-ethyl-α-cyano-3,4-dimethoxybenzyl)-N'-ethoxycarbonyl piperazine | $C_{19}H_{27}N_3O_4$ HCl | 57.30 (56.88) | 6.79 (6.43) | 10.56 (10.09) | 110–113 (hydro-chloride) | None | 2210 |
| 39 | N-(α-cyano-3,4-dimethoxybenzyl)-N'-ethoxycarbonyl homopiperazine | $C_{18}H_{25}N_3O_4$ | — | — | 12.10 (11.36) | — | 5.15 | 2210 |
| 40 | N-(α-cyano-2,3,4-trimethoxybenzyl)-N'-ethoxycarbonyl homopiperazine | $C_{19}H_{27}N_3O_5$ | — | — | 11.13 (10.57) | — | 4.89 | 2200 |
| 41 | N-(α-cyano-2,3,4-trimethoxybenzyl)-N'-cinnamyl piperazine | $C_{24}H_{29}N_3O_3$ HCl | 64.92 (64.84) | 6.81 (6.87) | 9.47 (9.34) | 169–174 (hydro-chloride) | 4.99 | 2210 |
| 42 | N-(α-cyano-3,4-dimethoxybenzyl)-N'-(4'-methoxycinnamyl)-piperazine | $C_{24}H_{29}N_3O_3$ HCl | 64.92 (65.08) | 6.81 (6.91) | 9.47 (9.52) | 203–206 (hydro-chloride) | — | 2210 |
| 43 | N-(α-cyano-3,4-dimethoxybenzyl)-N'-(2',3',4'-trimethoxycinnamyl)piperazine | $C_{26}H_{33}N_3O_5$ -$C_6H_3N_3O_7$ (Picrate) | — | — | 12.06 (13.31) | ca. 115–120 (Picrate) | — | 2210 |
| 44 | N-(α-cyano-3,4-dimethoxybenzyl)-N'-cinnamyl homopiperazine N-(α-cyano-2,3,4- | $C_{24}H_{29}N_3O_2$ | 73.62 (74.10) | 7.47 (7.93) | 10.73 (10.55) | 100–103 | 5.17 | 2230 |

-continued

| Example No. | Compounds | Formula | C | H | N | Melting Point (°C) | NMR (τ in CDCl₃) >CH—CN | IR (cm⁻¹) νC≡N |
|---|---|---|---|---|---|---|---|---|
| 45 | trimethoxybenzyl)-N'-cinnamyl homopiperazine | $C_{25}H_{31}N_3O_3$ HCl | 65.50 (65.18) | 6.99 (7.33) | 9.17 (9.01) | — | 4.92 | 2220 |
| 46 | N-(α-ethyl-α-cyano-3,4-dimethoxy)-N'-cinnamylpiperazine | $C_{25}H_{31}N_3O_2$ HCl | 67.87 (68.41) | 7.24 (7.51) | 9.50 (9.59) | ca. 270 (decomposition) (hydrochloride) | None | 2210 |
| 47 | N-(α-cyano-3,4-dimethoxybenzyl)-N'-diethylaminocarbonyl-methylpiperazine | $C_{20}H_{30}N_4O_3$ | 64.14 (64.31) | 8.08 (8.40) | 14.96 (15.12) | 130–131 | 5.17 | 2200 |
| 48 | N-(α-cyano-3,4-dimethoxybenzyl)-N'-pyrrolidinocarbonyl-methylhomopiperazine | $C_{21}H_{30}N_4O_3$ | — | — | 14.50 (13.99) | — | 5.16 | 2210 |
| 49 | N-(α-cyano-3,4-dimethoxybenzyl)-N'-aminocarbonylmethyl piperazine | $C_{16}H_{22}N_4O_3$ | 60.36 (60.23) | 6.97 (6.81) | 17.60 (17.59) | 185–187 | — | 2210 |
| 50 | N-(α-ethyl-α-cyano-3,9-dimethoxy-benzyl)-N'-diethyl-aminocarbonylmethyl piperazine | $C_{22}H_{34}N_4O_3$ HCL | 60.14 (59.78) | 7.97 (7.79) | 12.76 (12.31) | ca. 247 (decomposition) (hydrochloride) | None | 2200 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An α-cyanoamine compound represented by the formula,

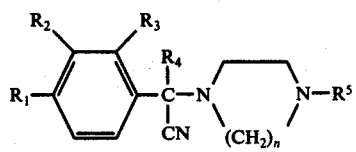

wherein $R_1$ is halogen or lower alkoxy; $R_2$ and $R_3$ are each hydrogen or lower alkoxy; $R_4$ is hydrogen or lower alkyl and $R_5$ is

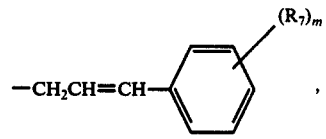

wherein $R_7$ is lower alkoxy and $m$ is a numeral from 0–3.

2. The α-cyanobenzylpiperazine of claim 1 which is N-(α-cyanobenzyl)-N'-cinnamylpiperazine represented by the formula,

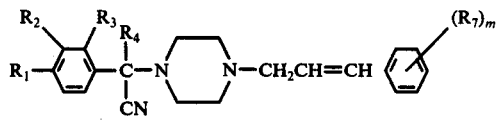

wherein $R_7$ is lower alkoxy, $m$ is a numeral 0–3 and $R_1$ to $R_4$ are the same as defined above.

3. The α-cyanoamine of claim 1 represented by the following formula,

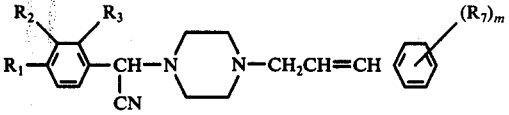

wherein $R_2$, $R_3$, $R_7$, $R_{12}$ and $m$ are the same as defined above.

4. The α-cyanoamine of claim 1 which is N-(α-cyano-3,4-dimethoxybenzyl)-N'-cinnamylpiperazine.

* * * * *